(12) United States Patent
Sugiyama

(10) Patent No.: US 8,591,400 B2
(45) Date of Patent: Nov. 26, 2013

(54) MEDICAL INSTRUMENT

(75) Inventor: Yuta Sugiyama, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 941 days.

(21) Appl. No.: 12/354,272

(22) Filed: Jan. 15, 2009

(65) Prior Publication Data

US 2009/0198104 A1  Aug. 6, 2009

(30) Foreign Application Priority Data

Jan. 31, 2008  (JP) .................................. 2008-021323

(51) Int. Cl.
*A61B 1/00* (2006.01)

(52) U.S. Cl.
USPC ........... 600/106; 600/103; 600/104; 600/117; 600/118; 600/145; 600/146

(58) Field of Classification Search
USPC ......... 600/103, 104, 106, 117, 118, 145, 146; 700/40, 45, 46, 52, 56–58, 63
See application file for complete search history.

(56) References Cited

U.S. PATENT DOCUMENTS

| | | | |
|---|---|---|---|
| 6,059,719 A | | 5/2000 | Yamamoto et al. |
| 7,931,586 B2 * | | 4/2011 | Brock et al. .................. 600/114 |
| 2002/0087048 A1 | | 7/2002 | Brock et al. |
| 2006/0287575 A1 | | 12/2006 | Onoda et al. |
| 2009/0018390 A1 * | | 1/2009 | Honda et al. .................. 600/106 |

FOREIGN PATENT DOCUMENTS

| | | | |
|---|---|---|---|
| CN | 1846600 A | 10/2006 | |
| EP | 1 870 016 A1 | 12/2007 | |
| JP | 57190541 | * 11/1982 | ............... A61B 1/00 |
| JP | 61-92650 | 5/1986 | |
| JP | 2004-129782 | 4/2004 | |
| JP | 2006-280627 | 10/2006 | |
| WO | WO 2006/035693 A1 | 4/2006 | |
| WO | WO 2007/011040 A1 | 1/2007 | |
| WO | WO 2007/080709 A1 | 7/2007 | |

OTHER PUBLICATIONS

Japanese Office Action dated Apr. 20, 2010.

* cited by examiner

*Primary Examiner* — Matthew J Kasztejna
*Assistant Examiner* — Kevin G Barry, III
(74) *Attorney, Agent, or Firm* — Scully, Scott, Murphy & Presser, P.C.

(57) ABSTRACT

A medical instrument, includes: an insertion section having a treatment instrument projection port and an active bending section at a position on the insertion section's proximal end portion side of the treatment instrument projection port; a joystick by which an operation of the active bending section is inputted; a driving section for driving the active bending section; and a control section for controlling the joystick and the driving section, and the control section having an active bending section which performs a control in one control mode selected from a plurality of different control modes.

15 Claims, 18 Drawing Sheets

$$V\alpha = K \frac{\theta\alpha}{\theta max} Vmax$$

MODE A1
$V\alpha$: K=1

MODE A2
$V\beta$: K=1/2

$$\phi 0 = \frac{\theta\alpha}{\theta max} \phi max$$

OUT = Kp × (φ0 − φd)

MODE D1
Kp=10

MODE D2
Kp=5

MODE E1

MODE E1

MODE E2

MODE E2

MEDICAL INSTRUMENT

This application claims the benefit of Japanese Application No. 2008-021323 filed in Japan on Jan. 31, 2008, the contents of which are incorporated herein by this reference.

BACKGROUND OF THE INVENTION

1. Field of the Invention

The present invention relates to a medical instrument, and particularly, relates to a medical instrument which includes: an elongated insertion section to be inserted into a subject, having a distal end portion provided with a treatment instrument projection port through which a treatment instrument is projected; and an active bending section.

2. Description of the Related Art

An endoscope is used for observation of organs in a body cavity by inserting its elongated insertion section into the body cavity, and to perform various treatments using a treatment instrument which is inserted through a channel in the treatment instrument. In the industrial field also, an endoscope can be used for observations and examinations of damage or corrosion in boiler, turbine, engine, or chemical plants by inserting its elongated insertion section in the inner portions of these units.

Such an endoscope has a bendable bending section connected to a distal end portion of the elongated insertion section. In order to bend the bending section of an endoscope, a so-called manually driven endoscope is widely used, and in using the endoscope, an operator operates a bending operation lever which is provided to an operation section thereof so as to directly pull or relax a wire that is inserted through the insertion section and is fixed to the bending section.

To the contrary, an electric endoscope is disclosed in Japanese Patent Application Laid-Open Publication No. 61-92650, the endoscope having an active bending section for pulling or relaxing a wire which is fixed to a bending section of the endoscope by a driving section such as a motor. In the electric endoscope, an operator operates a bending input section such as a joystick to input a direction for bending, or a speed for bending of an active bending section as an amount of bending for example. Then, the motor which is controlled based on the input amount of bending pulls/relaxes the bending operation wire, so that the bending section is operated to bend.

In the manually driven type endoscope, an operator variously changes the bending operation of the bending section without knowing. For example, while inserting the distal end portion of the endoscope to a target site in a body, or while observing a wide range for examination, an operator increases a speed for bending to achieve a quick insertion, and also considerably bends the portion, but while observing and performing various treatments using the treatment instrument inserted through a channel after the distal end portion is inserted to a target site, the operator decreases the bending speed, and also slightly and carefully bends the portion. Also, an operator variously changes the bending operation of the bending section without knowing, depending on the type of a treatment instrument inserted through the channel. For example, when the treatment instrument is a forceps, an operator quickly moves its bending section, and when the treatment instrument is an electric scalpel, an operator decreases the speed and carefully moves the scalpel. That is, the bending section of an endoscope is used in completely different manners for insertion and for treatment. In this way, in the case of a manually driven-type endoscope, an operator significantly changes the way to use the bending section, in other words, the bending operation, for insertion and for treatment, so as to ensure the accuracy of the treatment, and also reduce the time required for a treatment and the burden to a patient.

In the case of electric endoscope also, an operator can change the bending speed by an operation input section such as a joystick. For example, in many cases, a larger inclination of a joystick causes a higher bending speed, and a slighter inclination causes a lower bending speed.

SUMMARY OF THE INVENTION

According to the present invention, a medical instrument having an active bending section which enables an efficient treatment is attained.

In order to achieve the above object, a medical instrument according to the present invention includes: an elongated insertion section to be inserted into a subject, which is provided with a treatment instrument insertion port at the proximal end portion of the insertion section through which a treatment instrument is inserted, a treatment instrument projection port at the distal end portion of the insertion section through which the treatment instrument is projected out, and an active bending section at a position on the proximal end portion side of the treatment instrument projection port at the distal end portion; an input section for inputting an operation of the active bending section; a driving section for driving the active bending section based on an operation signal from the input section; and a control section for controlling the driving section and the input section, the control section performing a control in one control mode selected from a plurality of different control modes.

DETAILED DESCRIPTION OF THE PREFERRED EMBODIMENTS

First Embodiment

Now, with reference to the drawings, an endoscope apparatus 1 which is a first embodiment of a medical instrument according to the present invention will be explained below.
<Configuration of Endoscope Apparatus>

Figure 1:
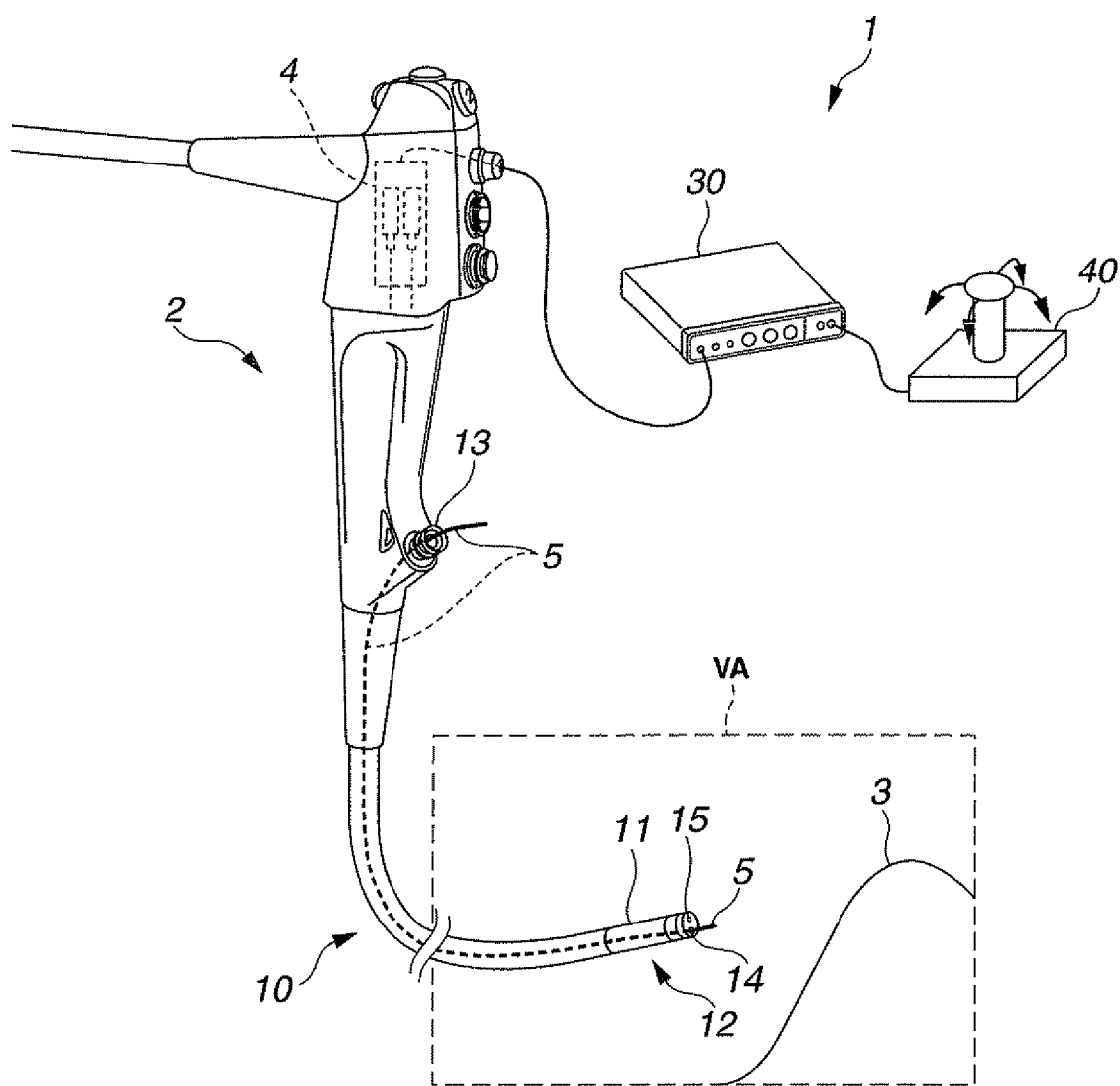
FIG. 1 is a configuration view showing an endoscope apparatus according to a first embodiment.
Figure 2A:
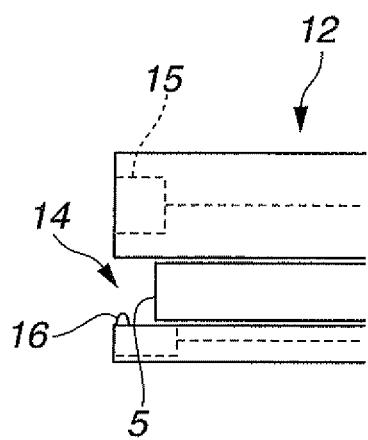
FIG. 2A is a cross-sectional view showing a distal end portion of the electric endoscope according to the first embodiment.
Figure 2B:
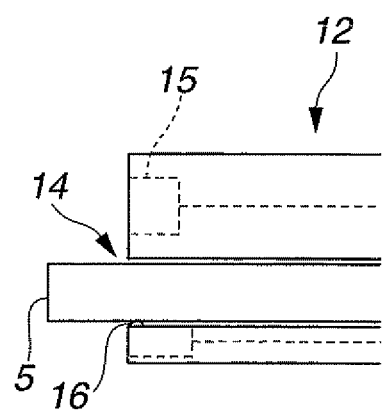
FIG. 2B is a cross-sectional view showing the distal end portion of the electric endoscope according to the first embodiment.
Figure 3A:
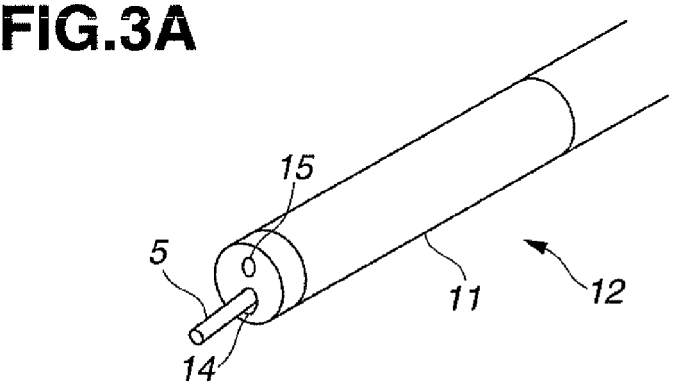
FIG. 3A is a perspective view illustrating a movement of an active bending section of the electric endoscope according to the first embodiment.
Figure 3B:
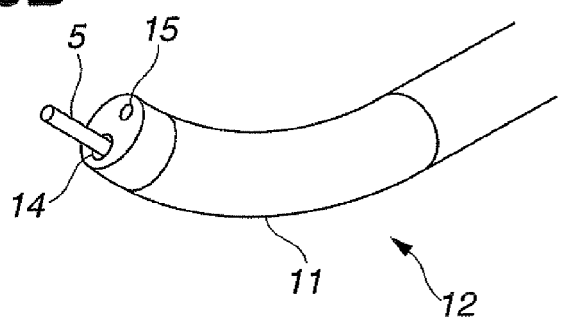
FIG. 3B is a perspective view illustrating a movement of an active bending section of the electric endoscope according to the first embodiment.
Figure 3C:
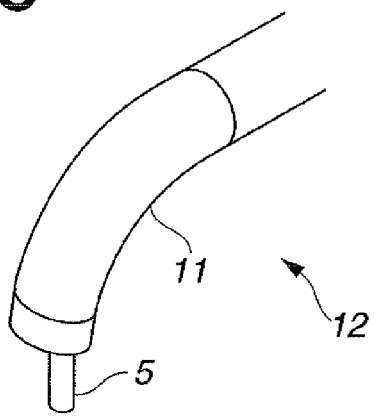
FIG. 3C is a perspective view illustrating a movement of an active bending section of the electric endoscope according to the first embodiment.
Figure 3D:
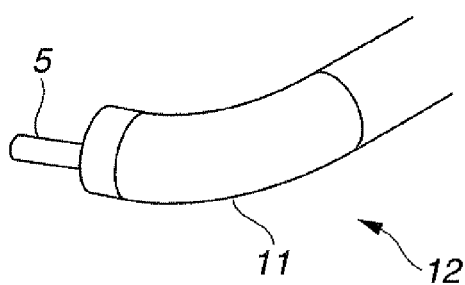
FIG. 3D is a perspective view illustrating a movement of an active bending section of the electric endoscope according to the first embodiment.
Figure 3E:
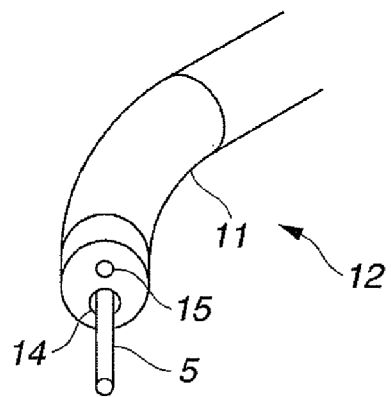
FIG. 3E is a perspective view illustrating a movement of an active bending section of the electric endoscope according to the first embodiment.

First, with FIG. 1, FIG. 2A, and FIG. 2B, the endoscope apparatus 1 according to the present embodiment will be explained below. FIG. 1 is a configuration view showing the endoscope apparatus 1 according to the present embodiment, and FIG. 2A and FIG. 2B are cross-sectional views showing a distal end portion 12 of an electric endoscope 2 according to the first embodiment. The endoscope apparatus 1 includes: the electric endoscope 2 having an active bending section 11 at the distal end portion 12 of an elongated insertion section 10 to be inserted to VA of a subject; a joystick 40 which is the input section with which an operator inputs an operation of the active bending section 11; a driving section 4 which is the driving section for driving the active bending section 11; and a control section 30 which is the control section for controlling the joystick 40 and the driving section 4, and the insertion section 10 has a channel therein through which a treatment instrument 5 is inserted from a treatment instrument insertion port 13 at a proximal end portion of the insertion section 11 and projects from a treatment instrument projection port 14 at the distal end portion 12. The active bending section 11 is disposed at a position on the proximal end portion side of the treatment instrument projection port 14.

The endoscope apparatus 1 has a CCD 15 at the distal end portion 12 of the insertion section 10 as an image pickup section, and is configured so that a picked up image of a target site 3 by the CCD 15 is displayed on a monitor (not shown) via a video processor (not shown).

The treatment instrument projection port 14 at the distal end portion 12 of the electric endoscope 2 according to the present embodiment is provided with a projection detection section for detecting a projection of the treatment instrument 5 from the treatment instrument projection port 14. The projection detection section is a switch 16 for example as shown in FIG. 2A and FIG. 2B. When the small switch 16 disposed at the channel near the treatment instrument projection port 14 is pressed by the treatment instrument 5 which is inserted through the channel as shown in FIG. 2B, the treatment instrument 5 detects the projection from the treatment instrument projection port 14. The projection detection section is not limited to the above switch 16, and may be various detection sections including a sensor such as a proximity sensor and an image detection section which detects a projection by processing an image of CCD, X-ray, ultrasound, CT, MRI, or the like.

The treatment instrument 5 is inserted in the treatment instrument insertion port 13 after the distal end portion 12 of the electric endoscope 2 is inserted to the target site 3 in the subject VA, or the distal end portion 12 is inserted to the target site 3 in the state with the treatment instrument 5 being completely received in the channel in the insertion section 10 of the electric endoscope 2. Then, at the point of time when a treatment to the target site 3 is started, the treatment instrument 5 is projected out from the treatment instrument projection port 14 for use.

Next, with FIG. 3A to FIG. 3E, movements of the active bending section 11 will be explained below. FIG. 3A to FIG. 3E are perspective views illustrating movements of the active bending section 11. As shown in FIG. 3A to FIG. 3E, the active bending section 11 is configured to be bendable in the four upward (FIG. 3B), downward (FIG. 3C), leftward (FIG. 3D), and rightward (FIG. 3E) directions. Of course, the active bending section 11 can be bendable in the diagonal directions by bending into the two directions which are orthogonal to each other at the same time.

A forward, backward, leftward, or rightward inclination of a lever 40A of the joystick 40 which is the input section for inputting operations of the active bending section 11 by an operator causes a direction in which the active bending section 11 bends to be inputted to the control section 30 as an upward, downward, leftward, or rightward bending direction operation signal. Also, for example, an inclination of the lever 40A from the vertical direction by an operator causes a bending speed operation signal which depends on the angle of the inclination to be inputted to the control section 30. The input section for inputting the operations of the active bending section 11 is not limited to the joystick 40, and may be other known input section such as master arm, keyboard, and mouse.

Figure 4A:
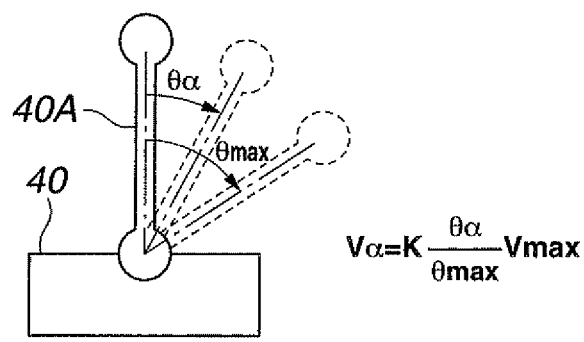
FIG. 4A is a side view illustrating an operation of a joystick according to the first embodiment.
Figure 4B:
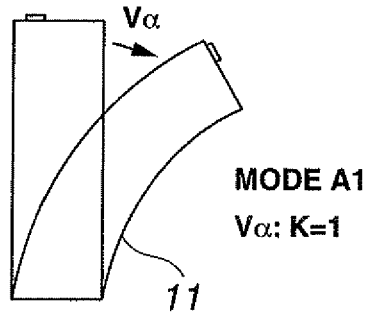
FIG. 4B is a side view illustrating an operation of the joystick according to the first embodiment.
Figure 4C:
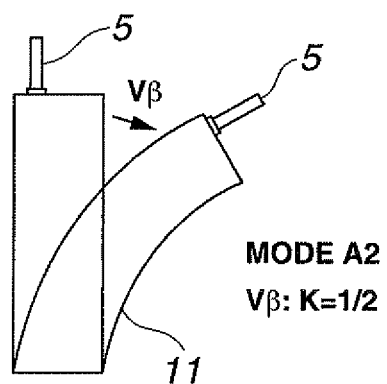
FIG. 4C is a side view illustrating an operation of the joystick according to the first embodiment.

Next, with FIG. 4A to FIG. 4C, operations of the joystick 40 will be explained below. FIG. 4A to FIG. 4C are side views illustrating the operations of the joystick 40. As shown in FIG. 4, assuming that when the lever 40A is inclined as the maximum inclination angle θmax which produces the maximum bending speed Vmax, for example, the bending speed Vα at the inclination angle θα is defined by the following formula:

$$V\alpha = K(\theta\alpha/\theta max) \times V max \qquad \text{(Formula 1)}$$

In the above formula 1, K is a parameter with respect to a bending speed which will be explained later, and the control modes having different parameters are different from each other.

The control section 30 outputs the signal outputted thereto from the joystick 40 as a drive signal to the driving section 4, and upon receiving the signal, the driving section 4 causes the active bending section 11 to be driven, that is, bended.

In the endoscope apparatus 1 according to the present embodiment, the driving section 4 is driven in a control mode selected by the control section 30 from a plurality of control modes for different driving speeds. The driving section 4 driven in any of the control modes for different driving speeds is driven at a driving speed which varies depending on a control mode even when the joystick 40 outputs the signal at an identical inclination angle θ to the control section 30.

Moreover, based on the signal from the switch 16 which is the projection amount detecting section, when the treatment instrument 5 projects from the treatment instrument projection port 14, the control section 30 of the endoscope apparatus 1 according to the present embodiment selects a control mode for a lower driving speed than that before the projection, and outputs a drive signal for a lower driving speed to the driving section 4. Conversely, when the treatment instrument 5 does not project from the treatment instrument projection port 14, the control section 30 selects a control mode for a higher driving speed than that after the projection, and outputs a drive signal for a higher driving speed to the driving section 4.

Figure 5:
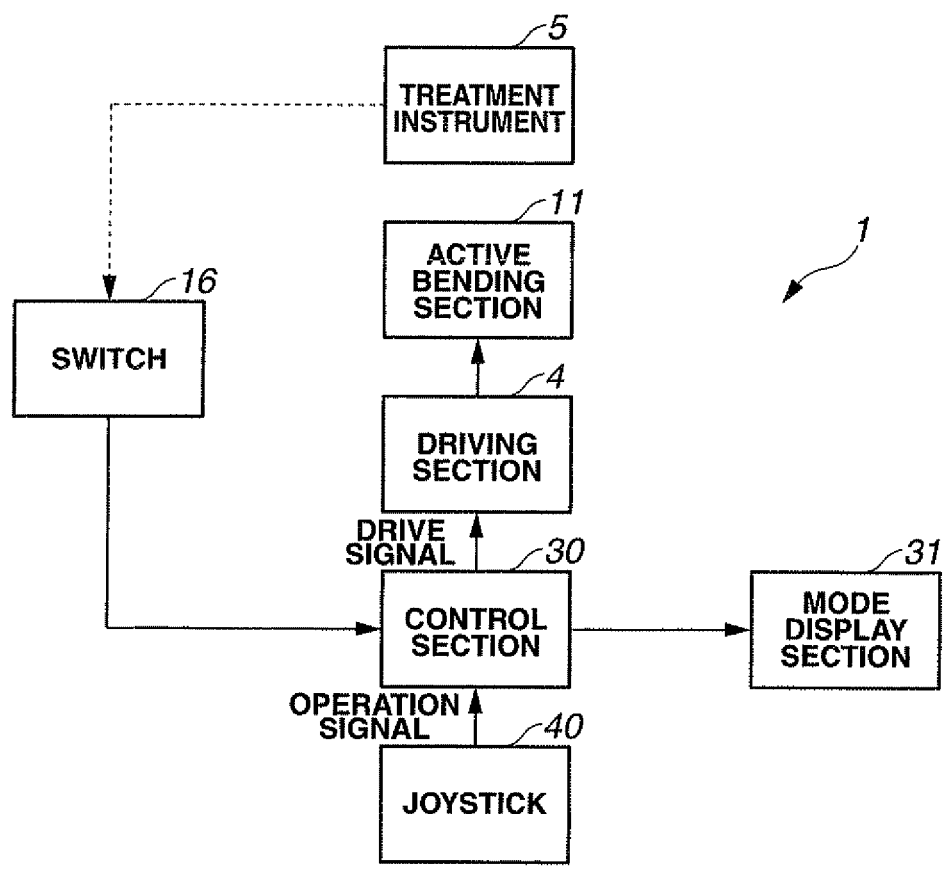
FIG. 5 is a block diagram showing a configuration of the endoscope apparatus according to the first embodiment.
Figure 6:
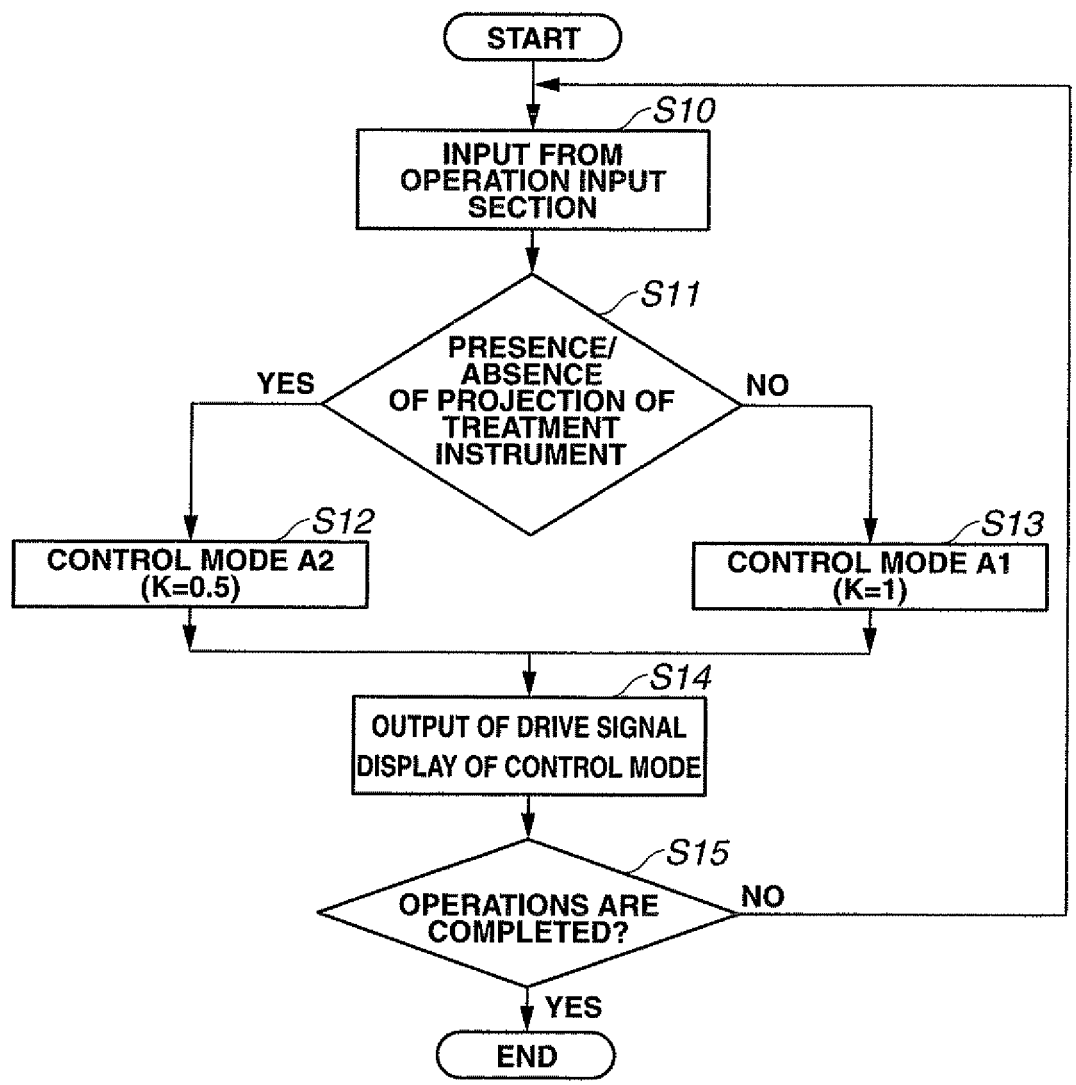
FIG. 6 is a flow chart illustrating a flow of the operations of a control section according to the first embodiment.

Now, with FIG. 4A to FIG. 4C, FIG. 5, and FIG. 6, operations of the control section 30 of the endoscope apparatus 1 will be explained below in detail. FIG. 5 is a block diagram showing a configuration of the endoscope apparatus 1, and FIG. 6 is a flow chart illustrating the flow of operations of the control section 30.

As shown in FIG. 5, the endoscope apparatus 1 is configured with the driving section 4 for driving the active bending section 11, the control section 30 for outputting a drive signal to the driving section based on a signal from the joystick 40, the switch 16 for detecting the presence/absence of projection of the treatment instrument 5 from the treatment instrument projection port 14, and a control mode display section 31 for displaying a control mode of the control section 30. The control mode display section 31 is the control mode display section for informing an operator of a control mode selected by the control section 30. The control mode display section may be LEDs that individually have a description of a control mode thereon, a display section for turning on an LED of a control mode selected by the control section 30, a display section for displaying a control mode name as well as an endoscope image on a monitor which displays an endoscope image, or the like. Hereinafter, as the control mode display section, a control mode display section 31 with LEDs will be used for explanation.

The control mode display section 31 allows an operator to check a control mode selected by the control section 30 before treatment, which improves the operability of the endoscope apparatus 1.

Next, with FIG. 6, the flow of operations of the control section 30 will be explained below. In the following explanation, only a bending speed of the active bending section 11 will be explained.

<Step S10>

An inclination of the lever 40A of the joystick 40 which is the operation input section by an angle θα by an operator causes an operation signal to be inputted from the joystick 40 to the control section 30.

<Step S11>

The switch 16 which is the projection detection section detects the presence/absence of the treatment instrument 5 from the treatment instrument projection port 14, and outputs the obtained detection information to the control section 30. Based on the detection information, the control section 30 of the endoscope apparatus 1 selects any of the two control modes A1 and A2.

<Step S12>

For the detection information indicating that the treatment instrument 5 is projecting from the treatment instrument projection port 14, the control section 30 of the endoscope apparatus 1 selects the control mode A2 based on the detection information. Herein, the control mode A2 is, as shown in FIG. 4C, a control mode with a parameter K for a bending speed being ½ or 0.5, which is called a treatment mode. The treatment mode is the control mode during a treatment In the treatment mode, the control section 30 outputs the following signal as a driving speed signal Vα2:

$$V\alpha 2 = 0.5 \times (\theta\alpha/\theta max) \times V max \qquad \text{(Formula 2)}$$

<Step S13>

For the detection information indicating that the treatment instrument 5 is not projecting from the treatment instrument projection port 14, the control section 30 of the endoscope apparatus 1 selects the control mode A1 based on the detection information. Herein, the control mode A1 is, as shown in FIG. 4B, a control mode with a parameter K for a bending speed being 1, which is called an insertion mode. That is, the insertion mode is the control mode during the insertion section 10 being inserted. In the insertion mode, the control section 30 outputs the following signal as a driving speed signal Vα1:

$$V\alpha 1 = 1 \times (\theta\alpha/\theta max) \times V max \qquad \text{(Formula 3)}$$

<Step S14>

The control section 30 of the endoscope apparatus 1 outputs the driving speed signal Vα1 or Vα2 to the driving section. As described above, Vα2=0.5×Vα, and the driving speed generated by the driving speed signal Vα2 in the case where the treatment instrument 5 is projecting from the treatment instrument projection port 14 is a half of that generated by the driving speed signal Vα1 in the case where the treatment instrument 5 is not projecting out, in other words, the input resolution of a moving speed of the joystick 40 in the treatment mode is twice that in the insertion mode.

Also, the control section 30 turns on an LED corresponding to the selected control mode A1 or A2 of the control mode display section 31.

<Step S16>

The control section 30 repeats the processes from Step S10 until the operations are not completed.

In the endoscope apparatus 1, even when the lever 40A of the joystick 40 is inclined at an identical angle θα, when the treatment instrument 5 is projecting from the treatment instrument projection port 14, the bending speed is automatically reduced to the half of that before the projection: in other words, when the treatment instrument 5 projects from the treatment instrument projection port 14, the endoscope apparatus 1 enables more precise adjustment of a bending speed and achieves the maximum bending speed of (½)Vmax by a wide movement of the lever 40A.

That is, the control section 30 selects one control mode from control modes for different driving speeds for an insertion of the insertion section 10 into the subject VA or an observation of the subject VA and for a treatment using the treatment instrument 5, and the control section 30 selects a control mode for a slower driving speed for a treatment using the treatment instrument 5 than that for the insertion of the insertion section 10 into the subject VA or the observation of the subject VA.

As a result, the endoscope apparatus 1 according to the present embodiment enables a quick insertion of the distal end portion 12 to the target site 3, and also, reduces a bending speed of the active bending section 11 for an identical operation of the joystick 140 in performing various treatments with the treatment instrument 5 projecting from the treatment instrument projection port 14, which facilitates a precise specification of speed, and improves the treatment accuracy and the operability of the apparatus.

Also, in the endoscope apparatus 1, even if an operator accidentally inclines the lever 40A of the joystick 40 by an excessive amount, the inclination can be easily corrected in performing a treatment because the active bending section 11 is bended at a slow bending speed.

Second Embodiment

Now, with reference to the drawings, an endoscope apparatus 1B which is a medical device of a second embodiment according to the present invention will be explained below. The endoscope apparatus 1B of the present embodiment has a basic configuration similar to that of the endoscope apparatus 1 of the first embodiment, and the same elements are designated by the same reference numerals and will not be explained below.

Figure 7:
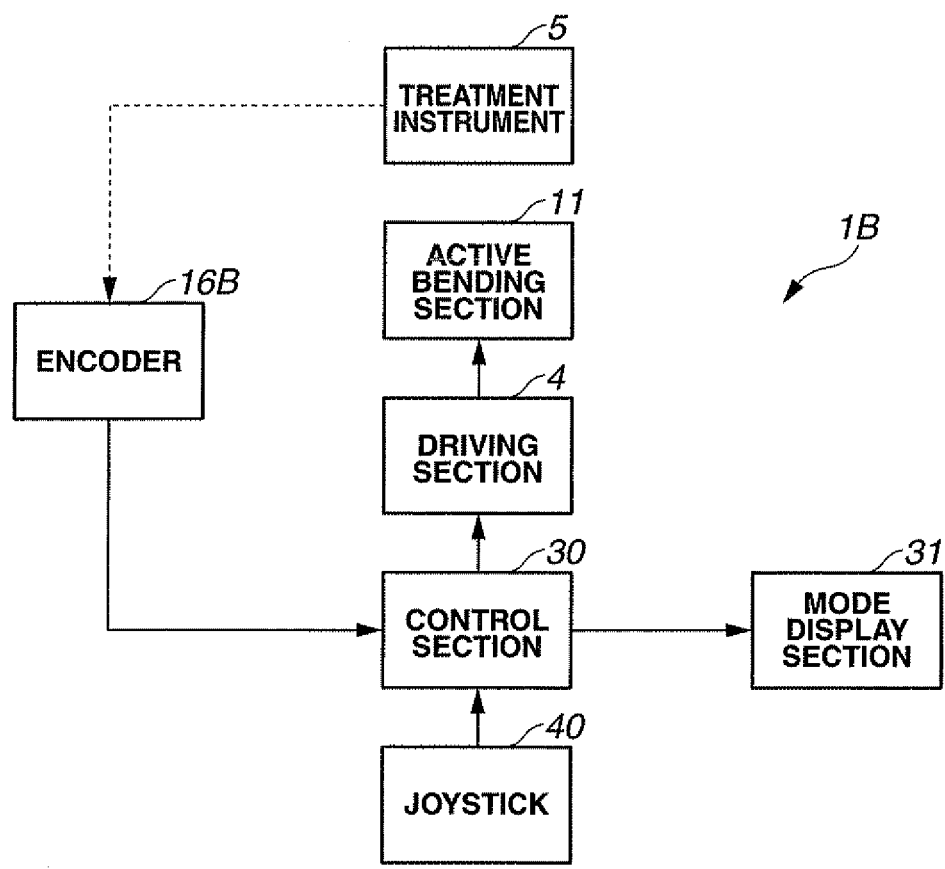
FIG. 7 is a block diagram showing a configuration of the endoscope apparatus according to a second embodiment.
Figure 8A:
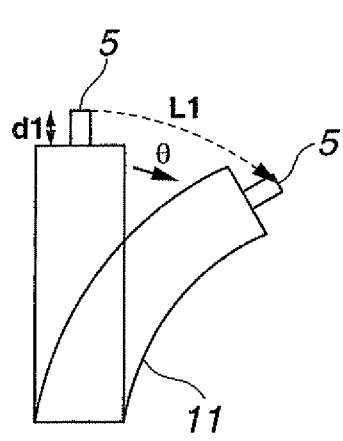
FIG. 8A is an exemplary view illustrating a difference of the movement amount of a distal end portion of a treatment instrument in accordance with a projection amount of the treatment instrument relative to the bending of the active bending section of the electric endoscope according to the second embodiment.
Figure 8B:
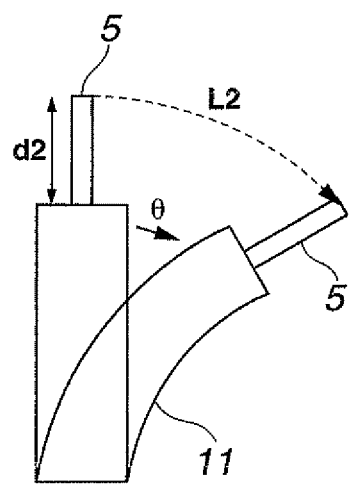
FIG. 8B is an exemplary view illustrating a difference of the movement amount of a distal end portion of a treatment instrument in accordance with a projection amount of the treatment instrument relative to the bending of the active bending section of the electric endoscope according to the second embodiment.
Figure 8C:
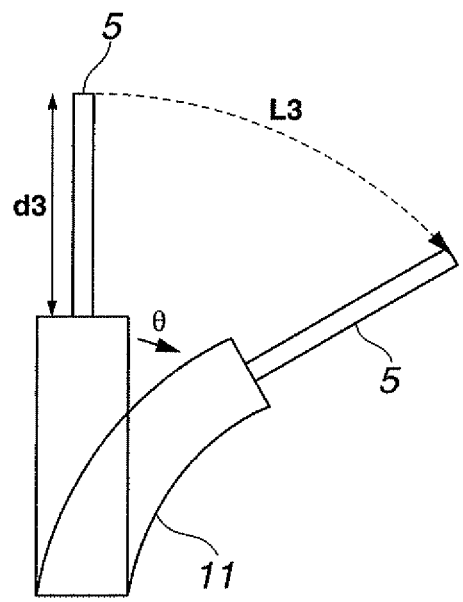
FIG. 8C is an exemplary view illustrating a difference of the movement amount of a distal end portion of a treatment instrument in accordance with a projection amount of the treatment instrument relative to the bending of the active bending section of the electric endoscope according to the second embodiment.
Figure 9:
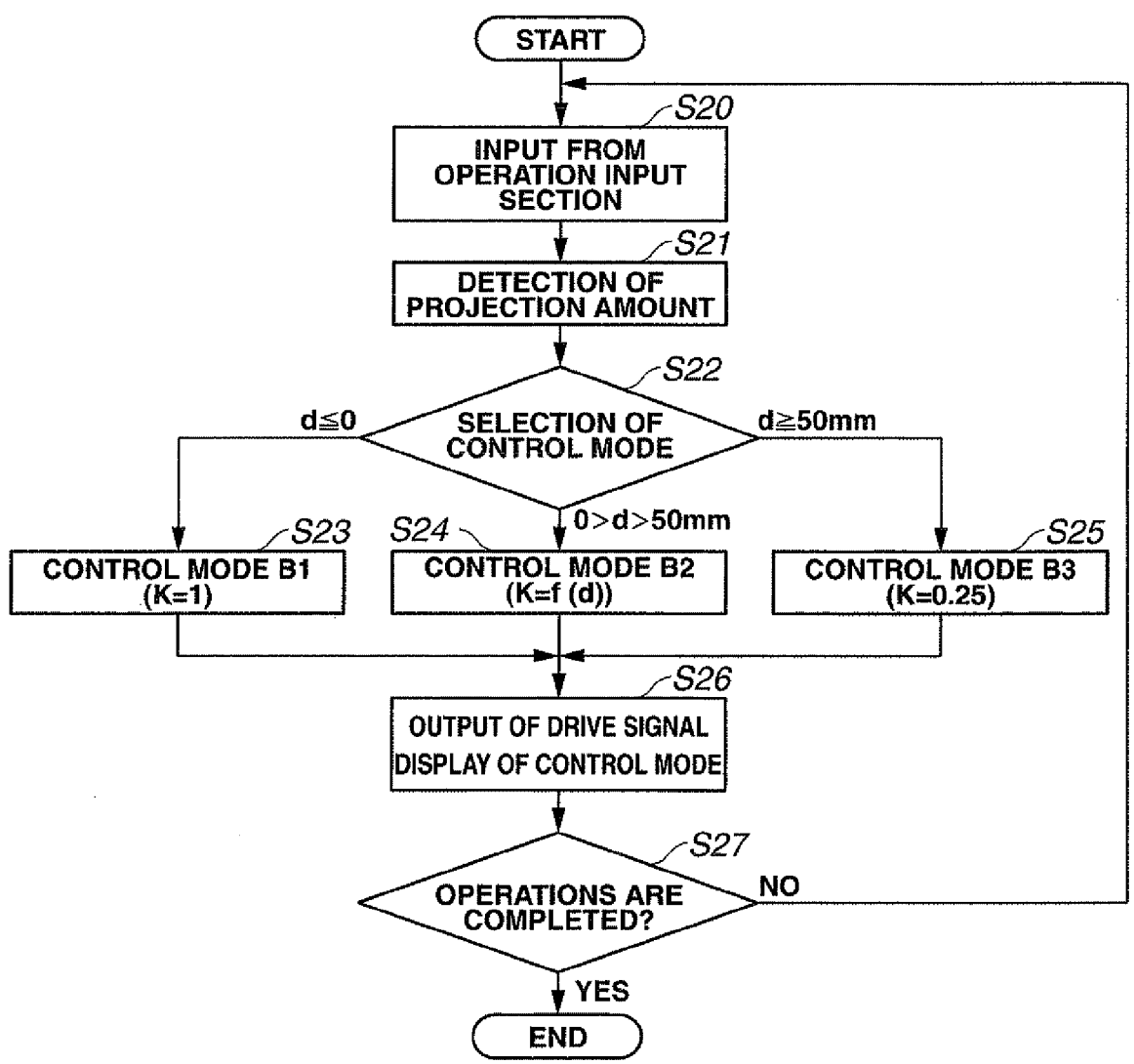
FIG. 9 is a flow chart illustrating a flow of operations of a control section according to the second embodiment.
Figure 10:
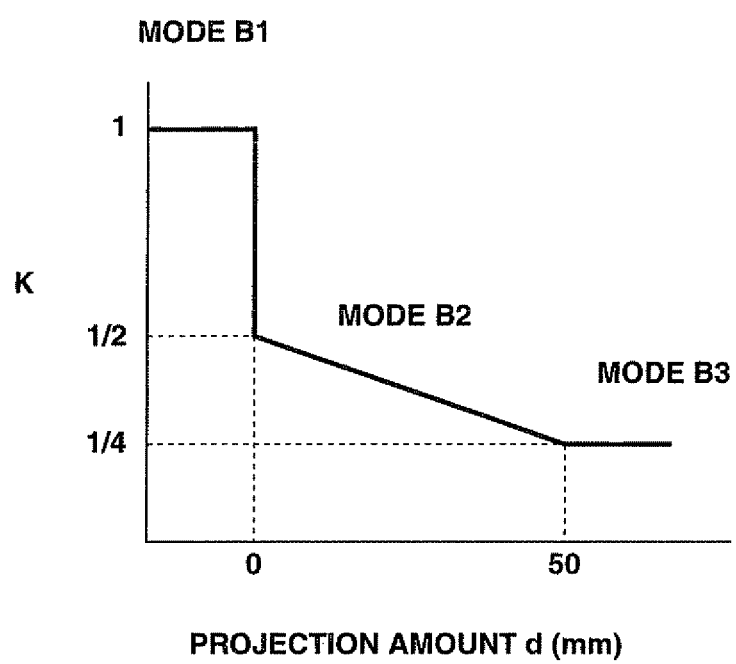
FIG. 10 is a graph illustrating a control mode of the control section according to the second embodiment.

FIG. 7 is a block diagram showing a configuration of the endoscope apparatus 1B of the present embodiment; FIG. 8A to FIG. 8C are exemplary views illustrating a difference of the movement amount of a distal end portion of the treatment instrument 5 in accordance with a projection amount d of the treatment instrument 5 from the treatment instrument projection port 14 relative to the bending of the active bending section; FIG. 9 is a flow chart illustrating the flow of operations of the control section 30 of the endoscope apparatus 1B; and FIG. 10 is a graph illustrating a control mode of the control section 30 of the endoscope apparatus 1B.

As shown in FIG. 7, the endoscope apparatus 1B is configured with: the driving section 4 for driving the active bending section 11; the control section 30 for outputting a drive signal to the driving section based on an operation signal from the joystick 40; an encoder 16B which is a projection amount detection section; and the control mode display section 31 for displaying a control mode of the control section 30.

The encoder 16B detects a projection amount of the treatment instrument 5 from the treatment instrument projection port 14, and for example measures the length of the treatment instrument 5 inserted in the treatment instrument insertion port 13 using a magnetic sensor near the treatment instrument insertion port 13 and a magnetic scale disposed in the longitudinal direction of the treatment instrument 5, and detects a projection amount based on the difference between the length of the inserted treatment instrument 5 and the length of the channel. The projection amount detection section is not limited to the above magnetic encoder 16B, and may be various detection sections including an optical encoder and an image detection section for detecting by processing an image of CCD, X-ray, ultrasound, CT, MRI, or the like.

Now, with FIG. 8A to FIG. 8C, the difference of a movement amount of the distal end portion of the treatment instrument 5 depending on the projection amount d of the treatment instrument 5 from the treatment instrument projection port 14 due to the bending of the active bending section 11 will be explained below. Even if the active bending section 11 is bended by an angle θ, as shown in FIG. 8A, with a small projection amount d1, the distal end portion of the treatment instrument 5 moves only a distance L1, but as shown in FIG. 8B, with a projection amount d2, the distal end portion of the treatment instrument 5 moves a distance L2, and as shown in FIG. 8C, with a large projection amount d3, the distal end portion of the treatment instrument 5 moves a distance L3. That is, the moving speed of the distal end portion of the treatment instrument 5 which actually performs treatment depends on not only a bending speed of the active bending section 11 but also a projection amount d.

Next, with FIG. 9, the flow of operations of the control section 30 will be explained below. In the following explanation, only a bending speed of the active bending section 11 will be explained.

<Step S20>

An inclination of the lever 40A of the joystick 40 which is the operation input section by an operator by an angle θα causes an operation signal to be inputted to the control section 30.

<Step S21>

The encoder 16B which is the projection amount detection section detects a projection amount of the treatment instrument 5 from the treatment instrument projection port 14, and the detection information is inputted to the control section 30.

<Step S22>

The control section 30 of the endoscope apparatus 1B selects any of the three control modes B1, B2, and B3 based on the detection information.

<Step S23>

For the detection information indicating that the treatment instrument 5 is not projecting from the treatment instrument projection port 14, that is, a projection amount d<=0, the control section 30 of the endoscope apparatus 1B selects the control mode B1 based on the detection information.

Herein, the control mode B1 is, as shown in FIG. 10, a control mode with a parameter K for a bending speed being 1. Therefore, the control section 30 of the endoscope apparatus 1B outputs the following signal as a driving speed signal Vβ1:

$$V\beta1 = 1 \times (\theta\alpha/\theta max) \times Vmax \quad \text{(Formula 4)}$$

<Step S24>

For the detection information indicating that the treatment instrument 5 is projecting from the treatment instrument projection port 14 with the projection amount d being 0<d<50 mm, the control section 30 of the endoscope apparatus 1B selects the control mode B2 based on the detection information.

Herein, the control mode B2 is a control mode with a parameter K for a bending speed being f(d), that is, a function of d. Therefore, the control section 30 of the endoscope apparatus 1B outputs the following signal as a driving speed signal Vβ2:

$$V\beta2 = f(d)(\theta\alpha/\theta max) \times Vmax \quad \text{(Formula 5)}$$

Herein, f(d) is, for example, as shown in FIG. 10, a linear function which is satisfied with K=0.5 when d=0, and K=0.25 when D=50 mm, and K within the range of 0<d<50 mm is represented by a straight line connecting the two points. That is, K decreases as the projection amount d increases.

<Step S25>

For detection information indicating that the projection amount d of the treatment instrument 5 from the treatment instrument projection port 14 is >=50 mm, the control section 30 of the endoscope apparatus 1B selects the control mode B3 based on the detection information.

Herein, the control mode B2 is a control mode with a parameter K for a bending speed being (¼). Therefore, the control section 30 outputs the following signal as a driving speed signal Vβ3:

$$V\beta3 = 0.25(\theta\alpha/\theta max) \times Vmax \quad \text{(Formula 6)}$$

<Step S26>

The control section 30 of the endoscope apparatus 1B outputs the driving speed signal Vβ1, Vβ2, or Vβ3 to the driving section 4. As described above, 0.5×Vα<Vβ2<0.25×Vα, or Vβ3=0.25×Vα. Therefore, the driving speed of the driving section 4 decreases or at least does not change as the projection amount d of the treatment instrument 5 from the treatment instrument projection port 14 increases.

In addition, the control section 30 turns on an LED of the control mode display section 31 which corresponds to the selected control mode B1, B2, or B3.

<Step S27>

The control section 30 repeats the processes from Step S20 until the operations are not completed.

The above described f(d) is a linear function, but is not limited to a linear function, and may be a formula having a trigonometrical function or other functional formula. The control section 30 in the above description selects a control mode for a slower moving speed in order from the three control modes as the projection amount d increases, but may select one of two control modes, or one from four or more control modes.

In the endoscope apparatus 1B, even for an identical inclination angle θα of the lever 40A of the joystick 40, a bending speed automatically changes depending on the projection amount d of the treatment instrument 5 from the treatment instrument projection port 14, that is as the projection amount d increases, and the bending speed decreases or at least does not change as the projection amount d increases.

As a result, the endoscope apparatus 1B according to the present embodiment has an advantage, in addition to the effect the endoscope apparatus 1 according to the first embodiment has, that even when the treatment instrument 5 considerably projects from the treatment instrument projection port 14, the distal end portion of the treatment instrument 5 does not widely move due to the projection. Therefore, in using the endoscope apparatus 1B, even when the treatment instrument 5 considerably projects from the treatment instrument projection port 14, an operator is able to precisely specify a speed, which improves accuracy of treatments and operability of the apparatus.

Third Embodiment

Now, with reference to the drawings, an endoscope apparatus 1C which is a medical device of a third embodiment according to the present invention will be explained below. The endoscope apparatus 1C of the present embodiment has a basic configuration similar to that of the endoscope apparatus 1 of the first embodiment, and the same elements are designated by the same reference numerals and will not be explained below.

Figure 11:
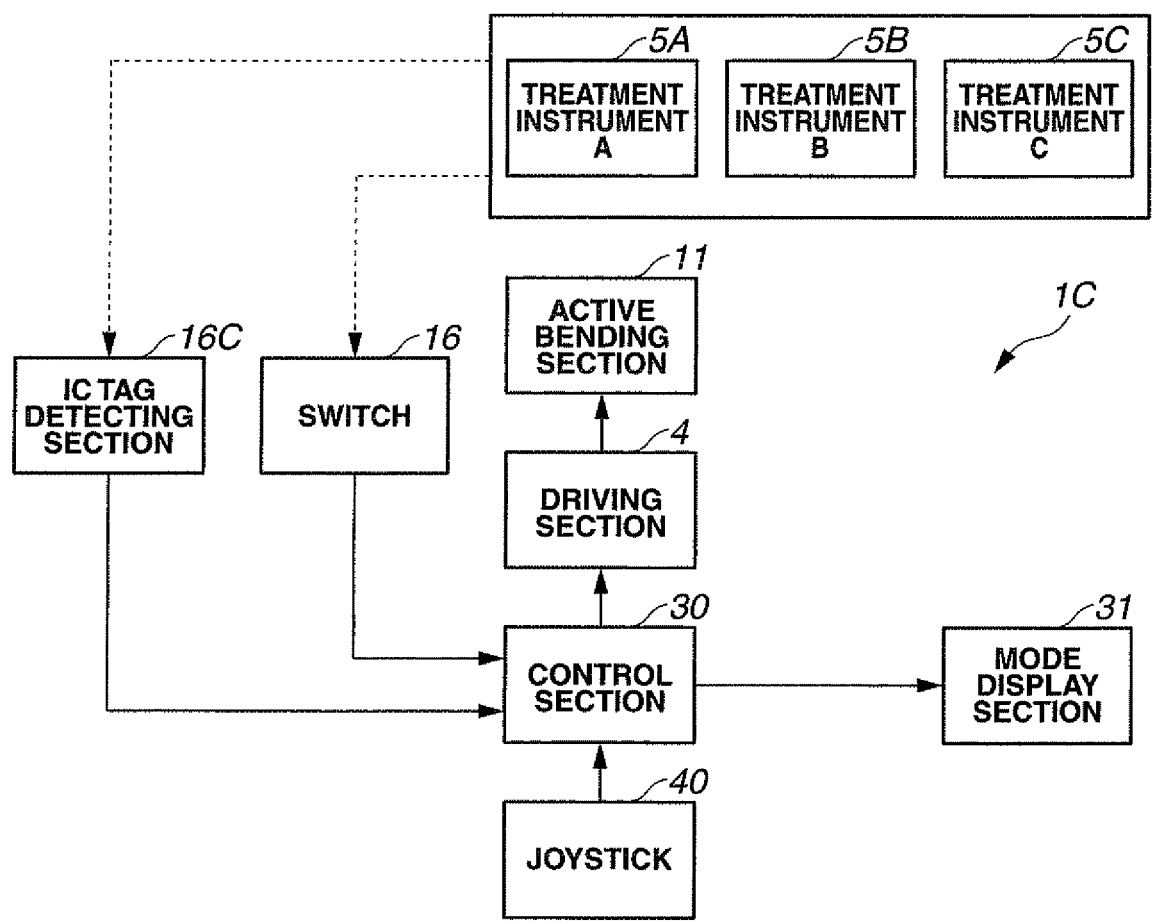
FIG. 11 is a block diagram showing a configuration of an endoscope apparatus according to a third embodiment.
Figure 12:
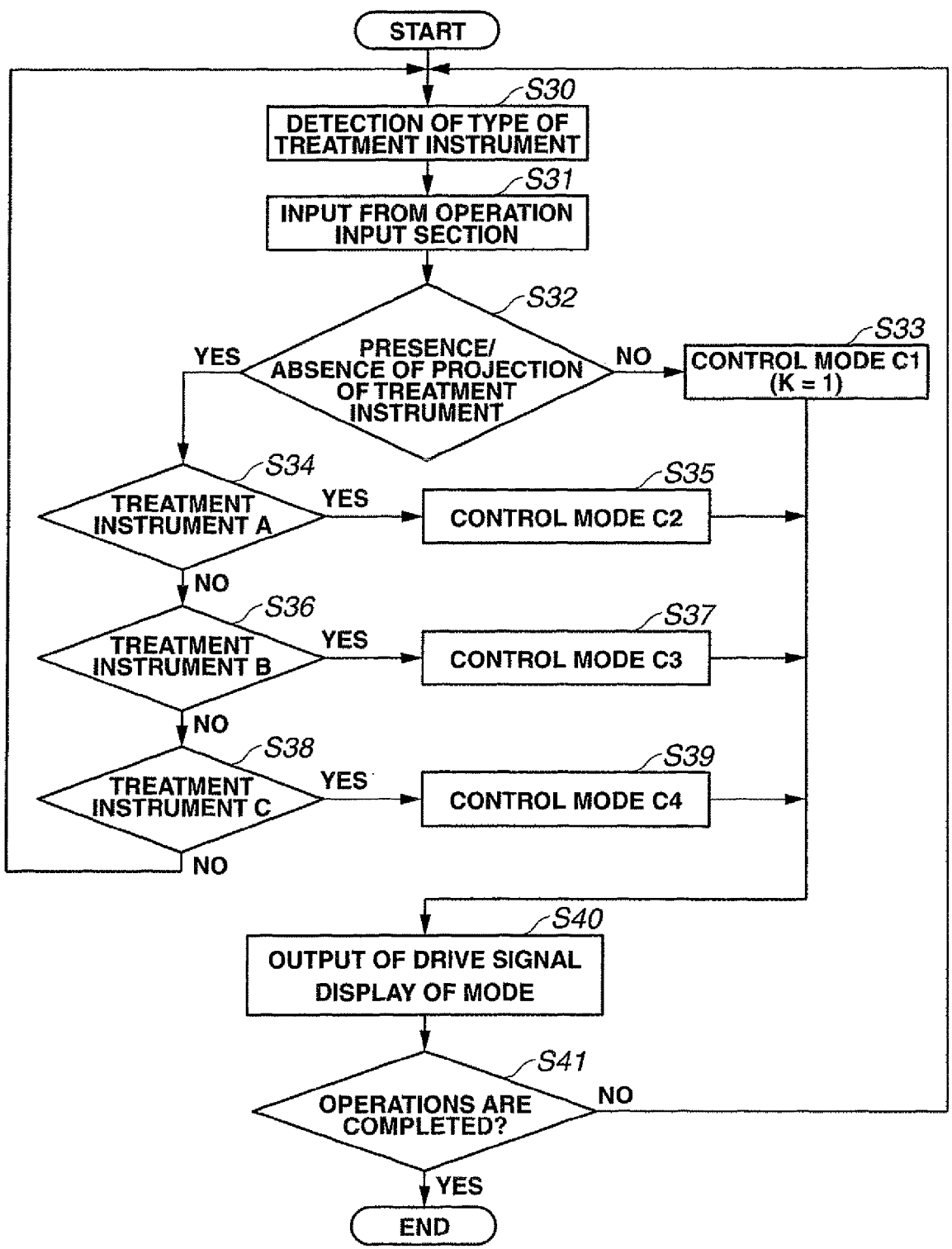
FIG. 12 is a flow chart illustrating a flow of operations of a control section according to the third embodiment.

FIG. 11 is a block diagram showing a configuration of the endoscope apparatus 1C of the present embodiment, and FIG. 12 is a flow chart illustrating the flow of operations of the control section 30.

As shown in FIG. 11, the endoscope apparatus 1C is configured with: the driving section 4 for driving the active bending section 11; the control section 30 for outputting a drive signal to the driving section based on a signal from the joystick 40; the switch 16 for detecting the presence/absence of a projection of the treatment instrument 5 from the treatment instrument projection port 14; an IC tag detecting section 16C which is a type detection section; and the control mode display section 31 for displaying a control mode of the control section 30.

Three types of treatment instruments 5A, 5B, and 5C can be inserted through the channel of the endoscope apparatus 1C, and each instrument is provided with an IC tag for identifying the type thereof. For example, the treatment instrument A is a grasping forceps having a large distal end portion; the treatment instrument B is a grasping forceps having a small distal end portion; and the treatment instrument C is a high-frequency electric scalpel.

The IC tag detecting section 16C is provided near the treatment instrument insertion port 13 for example, and detects the information of the IC tag which is disposed at the rear end or the like of the treatment instrument 5A, 5B, or 5C inserted through the channel, without contacting the tag. The type detection section is not limited to the IC tag detecting section, and may be a barcode reader, an identification tag detecting section having wireless communication capability, or the like.

Next, with FIG. 12, the flow of operations of the control section 30 will be explained below. In the following explanation, only a bending speed of the active bending section 11 will be explained.

<Step S30>

An insertion of the treatment instrument A, B, or C into the channel of the electric endoscope 2C from the treatment instrument insertion port 13 causes the IC tag detecting section 16C to detect the type of the treatment instrument, which is outputted to the control section 30 as treatment instrument type information.

<Step S31>

An inclination of the lever 40A of the joystick 40 which is the operation input section by an angle θα by an operator causes an operation signal to be inputted to the control section 30.

<Step S32>

The switch 16 which is the projection detection section detects the presence/absence of a projection of the treatment instrument 5 from the treatment instrument projection port 14, and outputs the detection information to the control section 30. The control section 30 selects a control mode based on the projection detection information.

<Step S33>

For the detection information indicating that the treatment instrument 5 is not projecting from the treatment instrument projection port 14, the control section 30 of the endoscope apparatus 1C selects the control mode C1 based on the detection information. The control mode C1 is a control mode with a parameter K for a bending speed being 1.

<Steps S34 and S35>

For the projection detection information indicating that the treatment instrument 5 is projecting from the treatment instrument projection port 14, the control section 30 of the endoscope apparatus 1C selects any of the control modes C2, C3, and C4 based on the treatment instrument type information. That is, for the treatment instrument type information indicating that the inserted instrument is the treatment instrument A, the control section 30 of the endoscope apparatus 1C selects the control mode C2. The control mode C2 is a control mode with a parameter K for a bending speed being 0.75.

<Steps S36 and S37>

For the treatment instrument type information indicating that the inserted instrument is the treatment instrument B, the control section 30 of the endoscope apparatus 1C selects the control mode C3. The control mode C3 is a control mode with a parameter K for a bending speed being 0.50.

<Steps S38 and S39>

For the treatment instrument type information indicating that the inserted instrument is the treatment instrument C, the control section 30 of the endoscope apparatus 1C selects the control mode C4. The control mode C4 is a control mode with a parameter K for a bending speed being 0.25.

For the treatment instrument type information indicating that the inserted instrument is none of the treatment instruments A, B, and C, the control section 30 goes back to Step S30 and rechecks the type of the treatment instrument.

<Step S40>

The control section 30 outputs a driving speed signal of individual control mode to the driving section.

Also the control section 30 turns on an LED corresponding to the selected control mode C1, C2, C3, or C4 of the control mode display section 31.

<Step S41>

The control section 30 repeats the processes from Step S10 until the operations are not completed.

In the endoscope apparatus 1C, even when the lever 40A of the joystick 40 is inclined at an identical angle θα, the bending speed is automatically different depending on the type of the treatment instrument 5. That is, the same operation of the joystick 40 by an operator facilitates the treatment instrument A which is a grasping forceps having a large distal end portion to move a relatively large distance, facilitates the treatment instrument B which is a grasping forceps having a small distal end portion to move relatively slowly, and facilitates the treatment instrument C which is a high-frequency electric scalpel to move finely. Namely, precise movements are required in using a treatment instrument such as a high-frequency electric scalpel which is used for tissue dissection or ablation, and instead of the precise movements, quick movements are required in using a treatment instrument for grasping, spraying, or the like, compared to the case with a treatment instrument such as a high-frequency electric scalpel.

Therefore, the endoscope apparatus 1C according to the present embodiment has an advantage, in addition to the effect the endoscope apparatus 1 according to the first embodiment has, that the apparatus 1C is able to perform a treatment at bending speed suitable to the type of the treatment instrument 5C, which improves accuracy of treatments and operability of the apparatus.

Modified Example 1 of Third Embodiment

Now, an endoscope apparatus 1C1 which is a medical instrument of modified example 1 of the third embodiment according to the present invention will be explained below. The endoscope apparatus 1C1 of the present modified example has a basic configuration similar to the endoscope apparatus 1C of the third embodiment, and the common elements will not be explained below.

The endoscope apparatus 1C1 of the present modified example has an electric endoscope 2C1 with an insertion section 10C1 in which two channels are provided, so that two treatment instruments can be inserted through the channels and be projected out from the distal end portion 12C1 to perform a treatment.

The endoscope apparatus 1C1 has the control section 30 to which information of the types of the two treatment instruments is inputted from the IC tag detecting section 16C, and then the control section 30 selects, based on the treatment instrument type information, a control mode having a smaller parameter K for a bending speed, that is a control mode for a slower bending speed. For example, in the case where a high-frequency electric scalpel and a grasping forceps are inserted at the same time through the channels, based on the treatment instrument type information of the high-frequency electric scalpel, the control section 30 selects a control mode. The control section 30 has priority selection information inputted therein in advance which specifies the treatment instrument type information to place a priority on in selecting a control mode.

The endoscope apparatus 1C1 selects a control mode for a treatment instrument having a higher order of priority among a plurality of treatment instruments, thereby an operator can perform a treatment more accurately, and the operability of the apparatus is improved.

Modified Example 2 of Third Embodiment

Now, an endoscope apparatus 1C2 which is a medical instrument of modified example 2 of the third embodiment according to the present invention will be explained below. The endoscope apparatus 1C2 of the present modified example has a basic configuration similar to the endoscope apparatus 1C of the third embodiment, and the common elements will not be explained below.

The endoscope apparatus 1C2 of the present modified example has an electric endoscope 2C2 with the treatment instrument insertion port 13. When a treatment instrument A, B, or C is inserted in the treatment instrument insertion port 13 through the channel of the electric endoscope 2C, the IC tag detecting section 16C which is an insertion detection section provided at the treatment instrument insertion port 13 detects the insertion of the treatment instrument to the treatment instrument insertion port, and simultaneously detects the type of the treatment instrument, which is outputted to the control section 30 as treatment instrument type information. Then, the control section 30 selects, in response to the type of the treatment instrument, a control mode for a moving speed corresponding to the type of the treatment instrument from control modes for different moving speeds, even if the treatment instrument 5 is not projecting from the treatment instrument projection port 14 yet. As a result, the operability of the apparatus is further improved when a treatment instrument is inserted and then displaced with another one for another treatment for example.

The endoscope apparatus 1C2 has an advantageous, in addition to the effect the endoscope apparatus 1C according to the third embodiment has, that the apparatus is easily assembled and has an improved operability because the IC tag detecting section 16C as the insertion detection section is provided at the treatment instrument insertion port 13.

In the above explanation, each of the endoscope apparatus 1 of the first embodiment, the endoscope apparatus 1B of the second embodiment, the endoscope apparatus 1C of the third embodiment, and the endoscope apparatuses 1C1 and 1C2 of the modified examples of the third embodiment has the control section 30 that selects a control mode from a plurality of control modes for different driving speeds of the driving section 4. The control section 30, however, may select a control mode according to not only a driving speed but also any of an operation torque, a bendable range, a control approach, and a degree of freedom, which achieves the effect of the present invention.

For example, for the detection information indicating that the treatment instrument 5 is projecting from the treatment instrument projection port 14, as compared to the case with the detection information indicating that the treatment instrument 5 is not projecting from the treatment instrument projection port 14, the control section 30 may select a control mode having a smaller operation torque or a smaller maximum angle, that is, a bendable range, by which the active bending section 11 is bendable. And as the result of that an operator is able to perform a treatment more safely and more accurately, and the operability of the apparatus is improved.

Alternatively, for example, for the detection information indicating that the treatment instrument 5 is not projecting from the treatment instrument projection port 14, the control section 30 may select PI (Proportional Integral) control as a control approach, and for the detection information indicating that the treatment instrument 5 is projecting from the treatment instrument projection port 14, the control section 30 may select more accurate PD (Proportional Differential) control, which allows an operator to perform a treatment more safely and more accurately, and improves the operability of the apparatus.

For an electric endoscope having a plurality of active bending sections at an insertion section, a control mode which limits the degree of freedom of each active bending section should be selected, which further improves the operability of the apparatus.

Fourth Embodiment

Now, with reference to the drawings, an endoscope apparatus 1D which is a medical instrument of a fourth embodiment according to the present invention will be explained below. The endoscope apparatus 1D of the present embodiment has a basic configuration similar to the endoscope apparatus 1 of the first embodiment, and the same elements are designated by the same reference numerals and will not be explained below.

Figure 13:
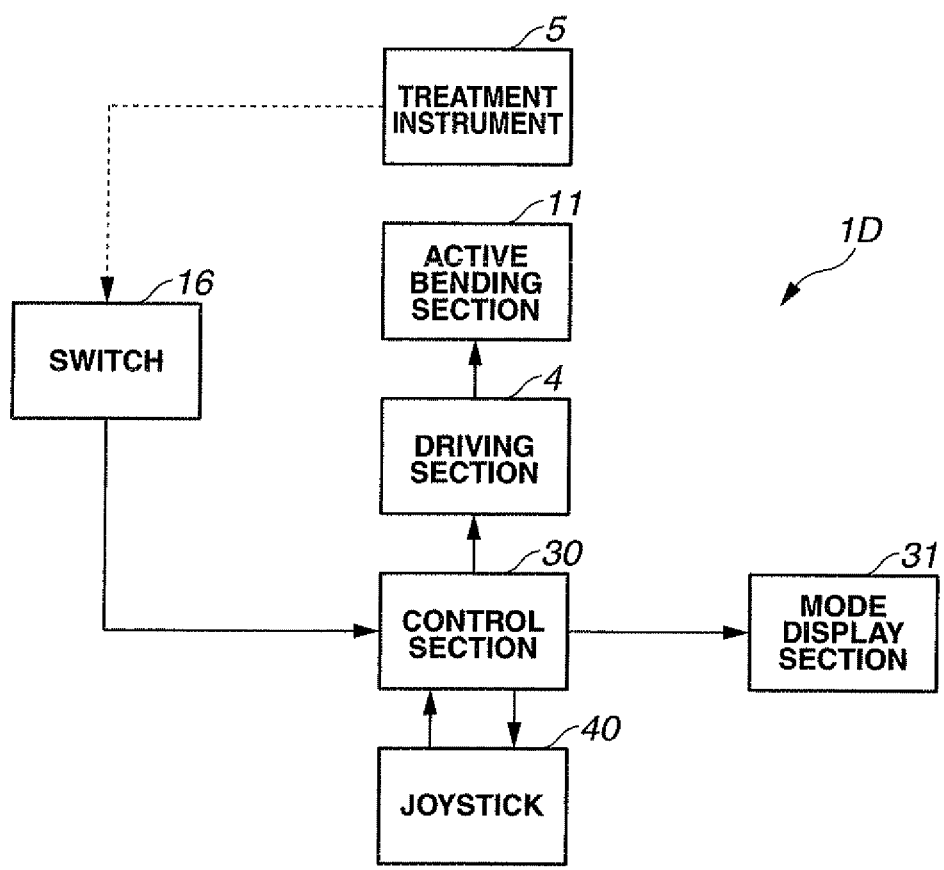
FIG. 13 is a block diagram showing a configuration of an endoscope apparatus according to a fourth embodiment.
Figure 14A:
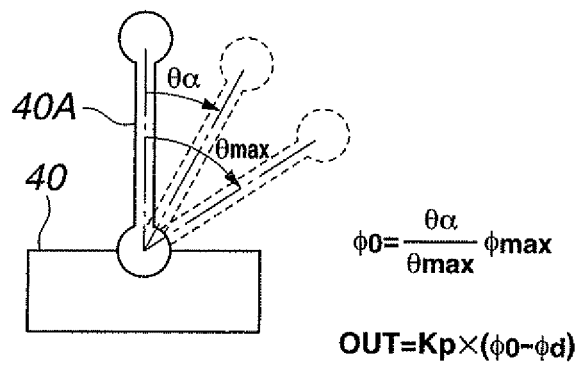
FIG. 14A is a flow chart illustrating a flow of operations of a control section according to the fourth embodiment.
Figure 14B:
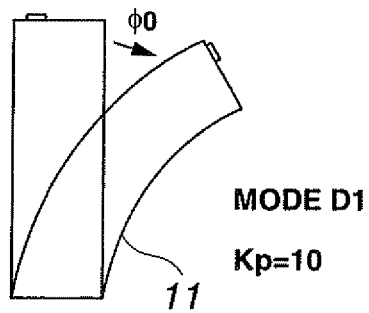
FIG. 14B is a flow chart illustrating a flow of operations of the control section according to the fourth embodiment.
Figure 14C:
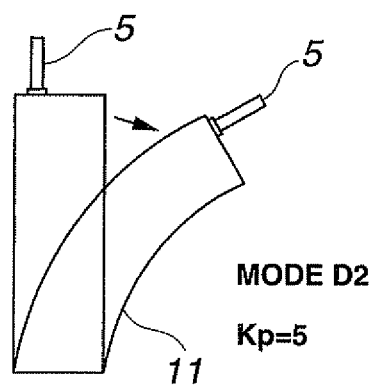
FIG. 14C is a flow chart illustrating a flow of operations of the control section according to the fourth embodiment.

FIG. 13 is a block diagram showing a configuration of the endoscope apparatus 1D of the present embodiment; and FIG. 14A to FIG. 14C are views illustrating the difference of the input operation of the control section 30 using the joystick 40.

As shown in FIG. 13, the endoscope apparatus 1D is configured with: the driving section 4 for driving the active bending section 11; the control section 30 for outputting a drive signal to the driving section based on a signal from the joystick 40, and controlling the joystick 40 which is the input section; a switch 16 which is the projection detection section; and the control mode display section 31 for displaying a control mode of the control section 30.

Unlike the endoscope apparatus 1 of the first embodiment, in the endoscope apparatus 1D, the control section 30 in different control modes controls the joystick 40 which is the input section, instead of the driving section 4. The joystick 40 of the endoscope apparatus 1D is configured so that an inclination angle $\theta$ of the lever 40A causes the active bending section 11 to be operated at the target bending angle.

As shown in FIG. 14A, when the inclination angle $\theta$ of the lever 40A is inputted, the joystick 40 controls the time for which the active bending section 11 is bended to a target displacement at the bending angle at a proportional gain Kp in proportion to the inclination angle $\theta$. For example, when the target displacement of the active bending section 11 is $\phi 0$, and the current displacement is $\phi d$, the operation signal outputted to the driving section 4 from the joystick 40 is expressed by the following formula:

$$\text{OUT} = Kp \times (\phi 0 - \phi d) \qquad \text{(Formula 7)}$$

And, the selection of a control mode of the joystick 40 in which an operation signal at different proportional gain Kp is outputted is performed by the control section 30.

That is, as shown in FIG. 14B, for the detection information that the treatment instrument 5 is not projecting from the treatment instrument projection port 14, the control section 30 of the endoscope apparatus 1D selects a control mode D1 based on the detection information. For example, the control mode D1 is a control mode with Kp=10. To the contrary, for the detection information that the treatment instrument 5 is projecting from the treatment instrument projection port 14, the control section 30 of the endoscope apparatus 1D selects a control mode D2 based on the detection information. For example, the control mode D2 is a control mode with Kp=5.

Since the control section 30 selects a different control mode depending on the presence/absence of the projection of the treatment instrument 5 from the treatment instrument projection port 14, the joystick 40 outputs an operation signal having a different response time to the control section 30 depending on the presence/absence of the projection of the treatment instrument 5 from the treatment instrument projection port 14. Herein, a response time is a time which is required for the active bending section to actually bend to form a target bending angle after an operator inclines the lever 40A of the joystick 40 by a predetermined angle corresponding to the target bending angle.

As a result, similar to the endoscope apparatus 1 according to the first embodiment, the endoscope apparatus 1D according to the present embodiment, enables a quick insertion of the distal end portion 12 to the target site 3, and also prolongs the response time of the active bending section 11 for the identical operation of the joystick 40 in performing various treatments with the treatment instrument 5 projecting from the treatment instrument projection port 14, which facilitates a precise specification of speed, and improves the treatment accuracy and the operability of the apparatus.

Modified Example of Fourth Embodiment

Now, with reference to the drawings, an endoscope apparatus 1D1 which is a medical instrument of a modified example of the fourth embodiment according to the present invention will be explained below. The endoscope apparatus 1D1 of the present modified example 1 has a basic configuration similar to the endoscope apparatus 1D of the fourth embodiment, and the same elements are designated by the same reference numerals and will not be explained below.

In the endoscope apparatus 1D1, the joystick 40 which is the input section is controlled by the driving section 4 in different control modes similar to the endoscope apparatus 1D of the fourth embodiment, but unlike the 1D, the joystick 40 is controlled in one control mode selected from a plurality of control modes having different ranges for detecting the joystick 40.

Figure 15A:
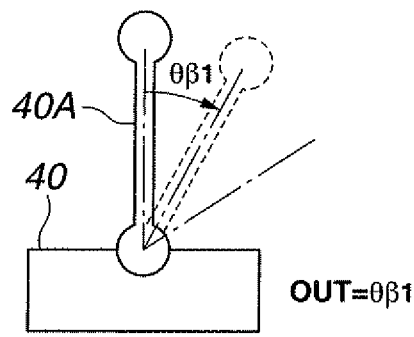
FIG. 15A is a side view illustrating a difference of detection range depending on a control mode of a joystick in a modified example of the fourth embodiment.
Figure 15B:
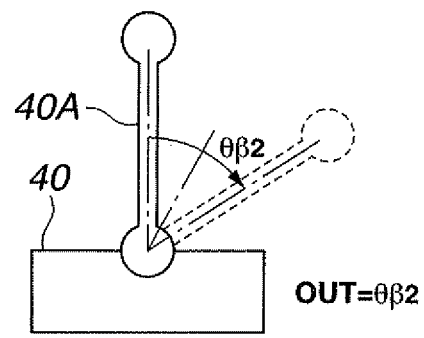
FIG. 15B is a side view illustrating a difference of detection range depending on a control mode of a joystick in a modified example of the fourth embodiment.
Figure 15C:
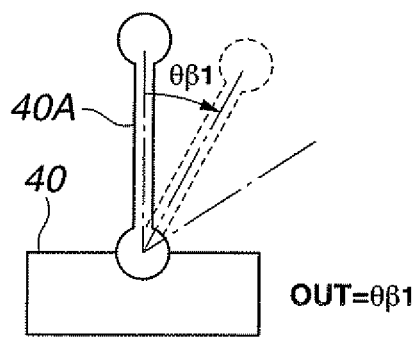
FIG. 15C is a side view illustrating a difference of detection range depending on a control mode of a joystick in a modified example of the fourth embodiment.
Figure 15D:
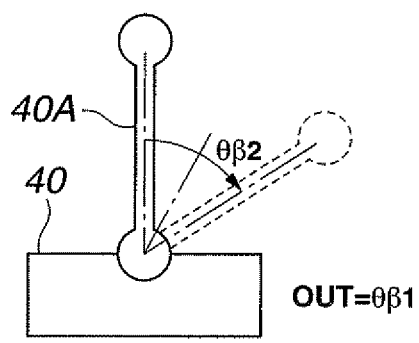
FIG. 15D is a side view illustrating a difference of a detection range depending on a control mode of a joystick in a modified example of the fourth embodiment.

FIG. 15A to FIG. 15D are side views illustrating the difference of the ranges for detecting the joystick 40 depending on the control mode of the present modified example. As shown in FIG. 15A, the joystick 40 controlled in a control mode E1 increases the signal outputted to the driving section 4 as the inclination angle of the lever 40A is increased from $\theta\beta1$ to $\theta\beta2$. However, as shown in FIG. 15B, by setting a detection range to be the angle $\theta\beta1$, the joystick 40 controlled in a control mode E2 does not change the operation signal outputted to the driving section 4 even when the lever 40A is inclined by the angle $\theta\beta2$ beyond the detectable angle $\theta\beta1$.

And for the detection information indicating that the treatment instrument 5 is not projecting from the treatment instrument projection port 14, the control section 30 of the endoscope apparatus 1D1 selects the control mode E1 based on the detection information. To the contrary, for the detection information indicating that the treatment instrument 5 is projecting from the treatment instrument projection port 14, the control section 30 of the endoscope apparatus 1D1 selects the control mode E2 based on the detection information.

As a result, similar to the endoscope apparatus 1D according to the fourth embodiment, the endoscope apparatus 1D1 according to the present modified example, enables a quick insertion of the distal end portion 12 to the target site 3, and also, due to the limited detection range of the joystick 40, prevents the active bending section 11 from moving at a high speed and to a wide range even when the joystick 40 is widely operated, in performing various treatments with the treatment instrument 5 projecting from the treatment instrument projection port 14, which improves the treatment accuracy and the operability of the apparatus.

In the above explanation, in the endoscope apparatus 1D of the fourth embodiment and the endoscope apparatus 1D1 of the modified example of the fourth embodiment, the control section 30 selects a control mode from a plurality of control modes having different response times or detection ranges of the joystick 40. The control section 30, however, may select a control mode of the joystick 40 according to not only a response time or detection range but also motion range or reaction force, which achieves the effect of the present invention.

For example, for the detection information indicating that the treatment instrument 5 is projecting from the treatment instrument projection port 14, the control section 30 may select a control mode having a small motion range, or a control mode having a large reaction force, so that an operator can accurately perform a treatment. The motion range is the maximum angle by which the lever 40A of the joystick 40 can be inclined, and can be physically limited by an electric stopper or the like. The reaction force is a force which is generated by the operation input section having a reaction force generating section, and is applied in the opposite direction to the direction an operator inputs an operation.

In addition, the treatment instrument 5 may be inserted through an overtube of the electric endoscope 2, instead of the channel of the electric endoscope 2. In the case, the configuration may be changed so that a projection from an opening provided in the overtube is detected instead of that from the treatment instrument projection port 14, for example.

Fifth Embodiment

Now, with reference to the drawings, an endoscope apparatus 1E which is a medical instrument of a fifth embodiment according to the present invention will be explained below. The endoscope apparatus 1E of the present embodiment has a basic configuration similar to the endoscope apparatus 1 of the first embodiment, and the same elements are designated by the same reference numerals and will not be explained below.

Figure 16:
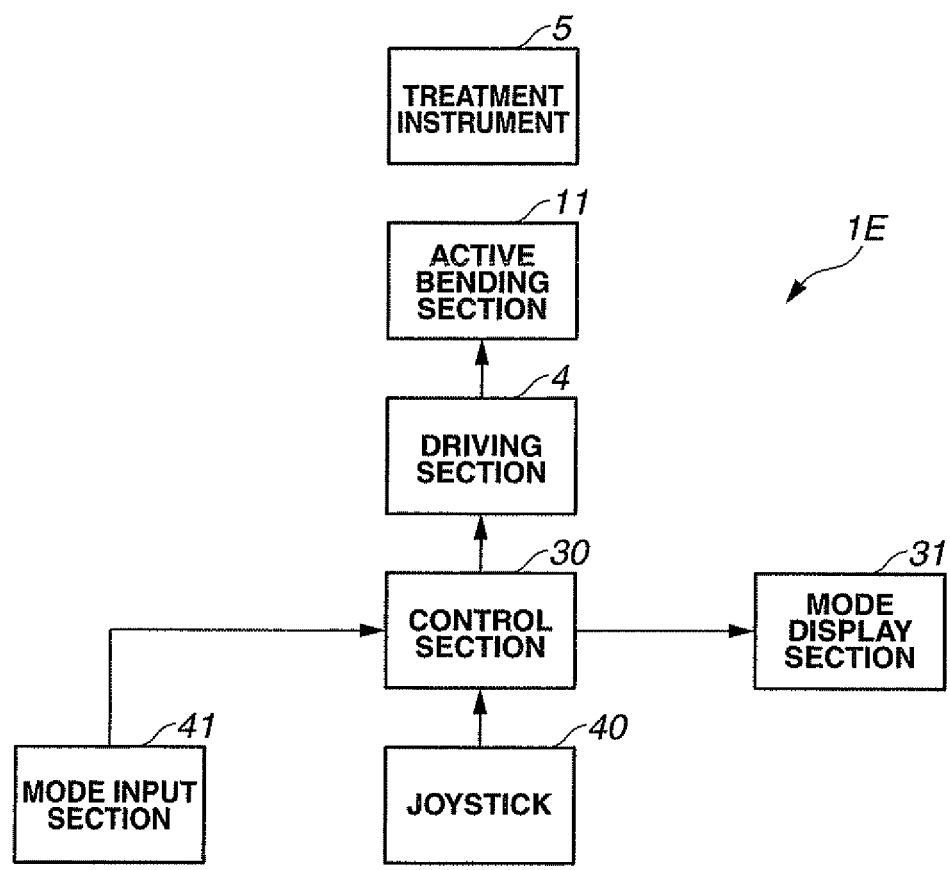
FIG. 16 is a block diagram showing a configuration of an endoscope apparatus according to a fifth embodiment.

FIG. 16 is a block diagram showing a configuration of the endoscope apparatus 1E of the present embodiment.

The endoscope apparatus 1E has a mode input section 41. Thus, in using the endoscope apparatus 1E, an operator is able to specify a control mode the control section 30 selects by inputting a command via the mode input section 41.

As a result, the endoscope apparatus 1E according to the present embodiment enables a quick insertion of the distal end portion 12 to the target site 3 in accordance with the operator's skill or the type of treatment, and also improves the treatment accuracy.

Sixth Embodiment

Now, with reference to the drawings, an active catheter apparatus 1F which is a medical instrument of a sixth embodiment according to the present invention will be explained below. The active catheter apparatus 1F of the present embodiment has a basic configuration similar to the endoscope apparatus 1 of the first embodiment, and the common elements will not be explained below.

Figure 17:
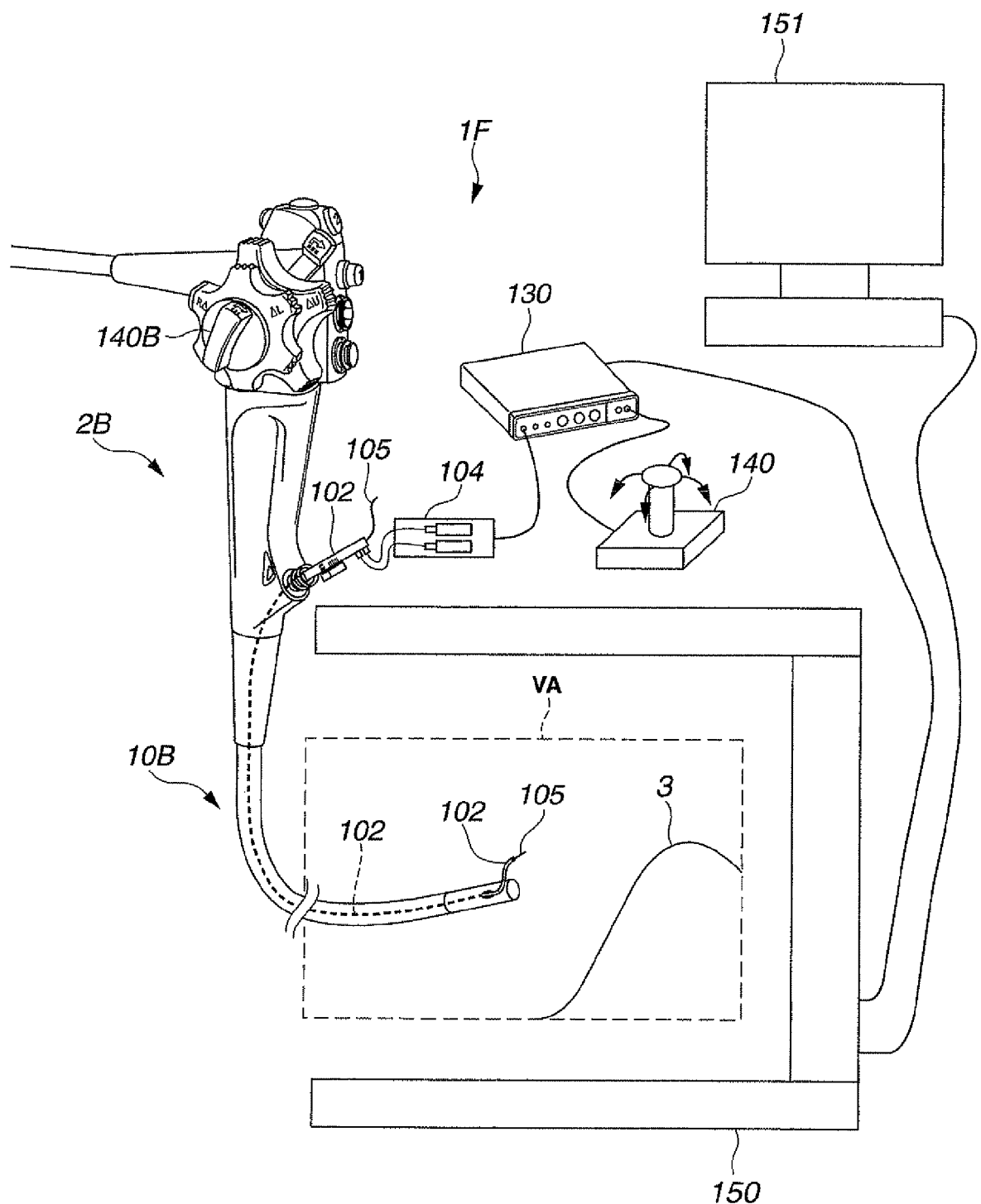
FIG. 17 is a configuration view showing a configuration of an active catheter apparatus according to a sixth embodiment.
Figure 18:
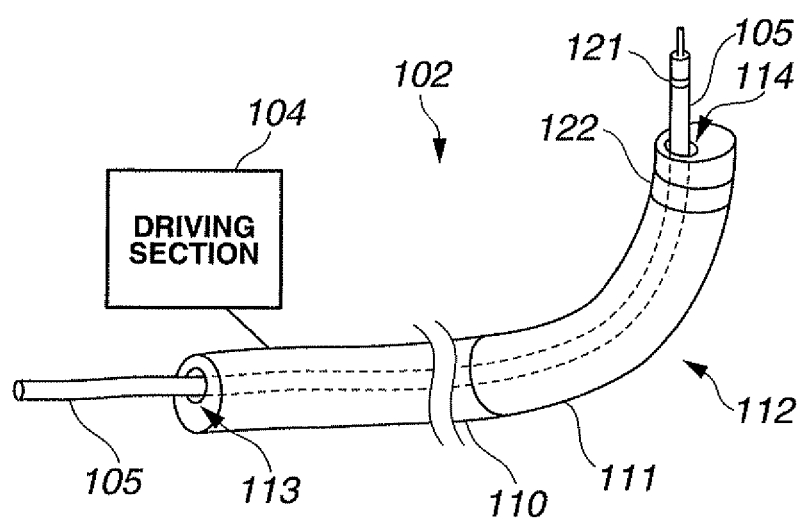
FIG. 18 is a perspective view illustrating a configuration of an active catheter according to the sixth embodiment.

FIG. 17 is a configuration view showing a configuration of the active catheter apparatus 1F of the present embodiment; and FIG. 18 is a perspective view illustrating a configuration of an active catheter 102 according to the present embodiment.

As shown in FIG. 17, the active catheter apparatus 1F includes: an active catheter 102 having an elongated insertion section 110 which is inserted into a subject VA; a joystick 140 which is the input section for inputting an operation of an active bending section 111 by an operator; a driving section 104 which is the driving section for driving the active bending section 111; and a control section 130 which is the control section for controlling the joystick 140 and the driving section 104. The insertion section 110 of the active catheter 102 includes a treatment instrument projection port 114 at the distal end portion 112 thereof, and the active bending section 111 at a position on the proximal end portion side of the treatment instrument projection port 114. The active catheter 102 includes a working lumen in the active catheter 102 so that a treatment instrument 105 is inserted in the working lumen from the treatment instrument insertion port 113 and projects from the treatment instrument projection port 114 at the distal end portion 112. The working lumen corresponds to the channel of the endoscope apparatus 1 of the first embodiment. The active catheter apparatus 1F further includes: an X-ray fluoroscopic apparatus 150 for checking the position of the active catheter 102 inserted into a living body; and an X-ray image display 151.

As shown in FIG. 17, the active catheter 102 is inserted into the channel of an insertion section 10B of the side-viewing endoscope 2B, and projects from the channel treatment instrument projection port at the distal end portion of the side-viewing endoscope 2B. Herein, the side-viewing endoscope 2B is a so-called manually driving endoscope in which an operator operates a bending operation lever 140B to directly pull and relax a wire for driving the bending section.

As shown in FIG. 18, the active catheter 102 is configured with an elongated insertion section 110 to be inserted into a subject, the insertion section 110 having treatment instrument projection port 114 from which the treatment instrument 105 projects at the distal end portion 112 thereof, and an active bending section 111 at a position on the proximal end portion side of the treatment instrument projection port 114. Also, the active catheter 102 includes the working lumen therein into which the treatment instrument 105 is inserted from the treatment instrument insertion port 113 and projects from the treatment instrument projection port 114. The active catheter 102 has an X-ray opaque chip 122 embedded at the distal end portion 112, and a catheter for local injection which is the treatment instrument 105 has an X-ray opaque chip 121 embedded at the distal end portion thereof.

An insertion of the active catheter 102 into a body is performed using the X-ray fluoroscopic apparatus 150 under X-ray fluoroscopy. The resulting X-ray image is also transmitted to the control section 130. In the active catheter apparatus 1F, the projection detection section for detecting the presence/absence of a projection of the treatment instrument 105 from the treatment instrument projection port 114 is an image-process detection section (not shown) for detecting a projection by image processing an X-ray image. The image-process detection section may be disposed in the control section 130. The image-process detection section acquires position information of the X-ray opaque chip 122 of the active catheter 102 and the X-ray opaque chip 121 of the treatment instrument 105 from the X-ray image. The position relationship of the chips is used to detect the presence/absence of a projection of the treatment instrument 105 from the treatment instrument projection port 114.

In the active catheter apparatus 1F, similar to the endoscope apparatus 1 of the first embodiment, based on the information of the projection detection section, when the treatment instrument 105 is projecting from the treatment instrument projection port 114, the control section 130 selects a control mode for a slower driving speed than that when the treatment instrument 105 is not projecting from the treatment instrument projection port 114.

As a result, the active catheter apparatus 1F according to the present embodiment enables a quick insertion of the distal end portion 112 to the target site 3, and also, reduces a bending speed of the active bending section 111 for an identical operation of the joystick 140 in performing various treatments with the treatment instrument 105 projecting from the treatment instrument projection port 114, which facilitates a precise specification of speed, and improves the treatment accuracy and the operability of the apparatus.

Modified Example of Sixth Embodiment

Now, an active catheter apparatus 1F1 which is a medical instrument of a modified example of the sixth embodiment according to the present invention will be explained below. The active catheter apparatus 1F1 of the present modified example has a basic configuration similar to the active catheter apparatus 1F of the sixth embodiment, and the common elements will not be explained below.

The active catheter apparatus 1F1 has an image-process projection amount detection section (not shown) for detecting a projection by image processing an X-ray image, as the projection amount detection section for detecting a projection amount of the treatment instrument 105 from the treatment instrument projection port 114.

In the active catheter apparatus 1F1, similar to the endoscope apparatus 1B which is the medical instrument of the second embodiment, based on the information obtained by the projection amount detection section, even for an identical inclination angle θα of the lever of the joystick 140, a bending speed automatically changes depending on the projection amount d of the treatment instrument 105 from the treatment instrument projection port 114, that is as the projection amount d increases, and the bending speed decreases or at least does not change as the projection amount d increases.

As a result, the active catheter apparatus 1F1 according to the present embodiment has an advantage, in addition to the effect the active catheter apparatus 1F according to the sixth embodiment has, that the distal end portion of the treatment instrument 105 does not move a large distance even when the treatment instrument 105 significantly projects from the treatment instrument projection port 114. Thus, the active catheter apparatus 1F1 facilitates a precise specification of a speed, and improves the treatment accuracy even when the treatment instrument 105 significantly projects from the treatment instrument projection port 114.

The present invention is not limited to be above described embodiments and modified examples, and for example, the endoscope apparatus 1 of the first embodiment may be provided with the mode input section of the endoscope apparatus 1E of the fifth embodiment so that an operator can select one of the two control sections. Also for example, the projection detection section of the endoscope apparatus 1B of the second embodiment may be used in the endoscope apparatus 1C of the third embodiment. Moreover, for example, a control mode for controlling a response speed and a control mode for controlling a reaction force may be simultaneously selected.

The control section controls both of the input section and the driving section as described above, but other control section may be used so that the control section for controlling the input section and the control section for controlling the driving section separately operate.

The embodiments of electric endoscopes and electric catheters have been explained, but the present invention is applicable to endoscopes which have an actively movable section using various known drive systems, such as an endoscope having a bending section which is driven by a pneumatic actuator, and is applicable to both of flexible endoscopes and rigid endoscopes.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A medical instrument, comprising:
   an elongated insertion section to be inserted into a subject, which is provided with a treatment instrument insertion port at a proximal end portion of the insertion section through which a treatment instrument, which is a separate body from the insertion section, is inserted, a treatment instrument projection port at a distal end portion of the insertion section through which the treatment instrument is projected out, and an active bending section at a position on the proximal end portion side of the treatment instrument projection port at the distal end portion;
   an input section for inputting an operation of the active bending section;
   a driving section for driving the active bending section based on an operation signal from the input section;
   a control section for controlling the driving section and the input section in one control mode selected from a plurality of different control modes; and
   a projection detection section, disposed at the distal end portion of the insertion section, for detecting the presence of a projection of the treatment instrument from the treatment instrument projection port, wherein
   the control section selects the one control mode based on the information from the projection detection section;
   the plurality of control modes are different from each other in driving speeds of the active bending section, and
   based on the information from the projection detection section, when a projection of the treatment instrument from the treatment instrument projection port is detected, the control section selects a control mode for a lower driving speed of the active bending section of the insertion section than a driving speed when the treatment instrument is not projecting from the treatment instrument projection port.

2. The medical instrument according to claim 1, wherein the control section controls the driving section in the one control mode selected from the plurality of different control modes which are different in any of operation torque, bending range, control approach, and degree of freedom.

3. The medical instrument according to claim 2, wherein the one control mode selected by the control section for an insertion of the insertion section into the subject or an observation of the subject is different from the one control mode selected by the control section for a treatment by the treatment instrument.

4. The medical instrument according to claim 3, wherein
the plurality of control modes are different from each other in driving speeds, and
the control section selects a control mode for a lower driving speed for a treatment by the treatment instrument than a driving speed for an insertion of the insertion section into the subject or an observation of the subject.

5. The medical instrument according to claim 1, wherein the control section controls the input section in the one control mode selected from the plurality of different control modes which are different in any of response time, detection range, movable range, and reaction force.

6. The medical instrument according to claim 1, further comprising:
an insertion detection section for detecting the presence/absence of an insertion of the treatment instrument into the treatment instrument insertion port, and
the control section selects the one control mode based on the information from the insertion detection section.

7. The medical instrument according to claim 1, further comprising:
a projection amount detection section for detecting a projection amount of the treatment instrument from the treatment instrument projection port, and
based on the information from the projection amount detection section, the control section selects the one control mode in accordance with the projection amount of the treatment instrument from the treatment instrument projection port.

8. The medical instrument according to claim 7, wherein
the plurality of control modes are different from each other in driving speeds, and
based on the information from the projection amount detection section, the control section selects a control mode for a lower driving speed as the projection amount of the treatment instrument from the treatment instrument projection port increases.

9. The medical instrument according to claim 1, further comprising:
a type detection section for detecting a type of the treatment instrument inserted in the treatment instrument insertion port, and
the control section selects the one control mode based on the information from the type detection section.

10. The medical instrument according to claim 1, further comprising a control mode input section.

11. The medical instrument according to claim 1 is an active endoscope apparatus.

12. The medical instrument according to claim 1 is an active catheter apparatus.

13. The medical instrument according to claim 12, wherein the active catheter is inserted through a channel of the insertion section of an endoscope.

14. The medical instrument according to claim 1, further comprising: a control mode display section for displaying the selected one control mode.

15. The medical instrument according to claim 1, wherein a bending speed of the active bending section is slower when an operation is input to the input section when projection of the treatment instrument from the treatment instrument projection port is detected than the bending speed of the active bending section when the same operation is input to the input section when the treatment instrument is not projected from the treatment instrument projection port.

* * * * *